United States Patent [19]

Van Cleave

[11] 4,073,937

[45] Feb. 14, 1978

[54] PREVENTIVE TREATMENT FOR OTITIS EXTERNAE

[76] Inventor: Jon Stephen Van Cleave, 812 SW. Lally St., Des Moines, Iowa 50315

[21] Appl. No.: 713,633

[22] Filed: Aug. 12, 1976

[51] Int. Cl.² .................... A61K 31/23; A61K 31/16; A61K 33/22; A61K 31/19
[52] U.S. Cl. ................................. 424/312; 424/130; 424/148; 424/317; 424/320; 424/343
[58] Field of Search ........................................ 424/312

[56] References Cited

U.S. PATENT DOCUMENTS 2,721,161  10/1955  Maiese ................................. 424/312

*Primary Examiner*—Frederick E. Waddell
*Attorney, Agent, or Firm*—Zarley, McKee, Thomte, Voorhees & Sease

[57] ABSTRACT

A preventive treatment for Otitis Externae, commonly referred to as "Swimmer's Ear", and for eliminating the discomfort of water remaining in the external canal, which comprises applying to the skin surface of the external auditory canal of a patient's ear, a pharmaceutically safe, liquid, nonionic, substantially water insoluble, aqueous surface tension reducing agent.

7 Claims, 5 Drawing Figures

U.S. Patent    Feb. 14, 1978    4,073,937
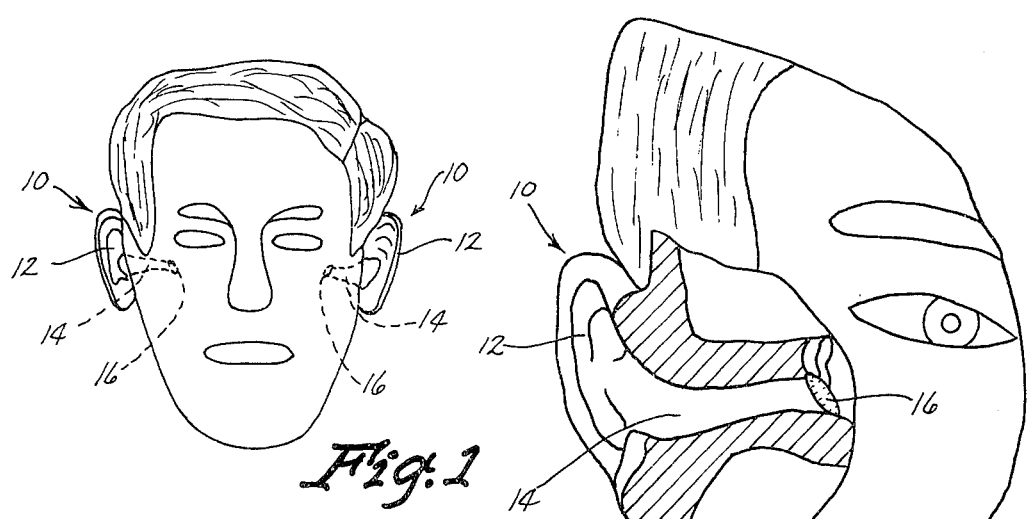
Fig. 1
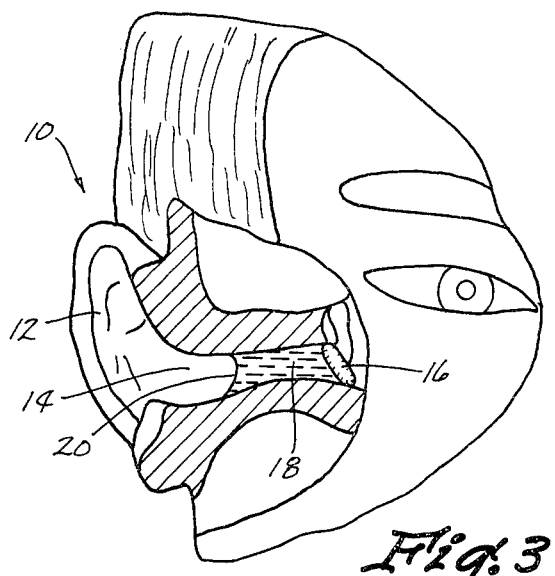
Fig. 2
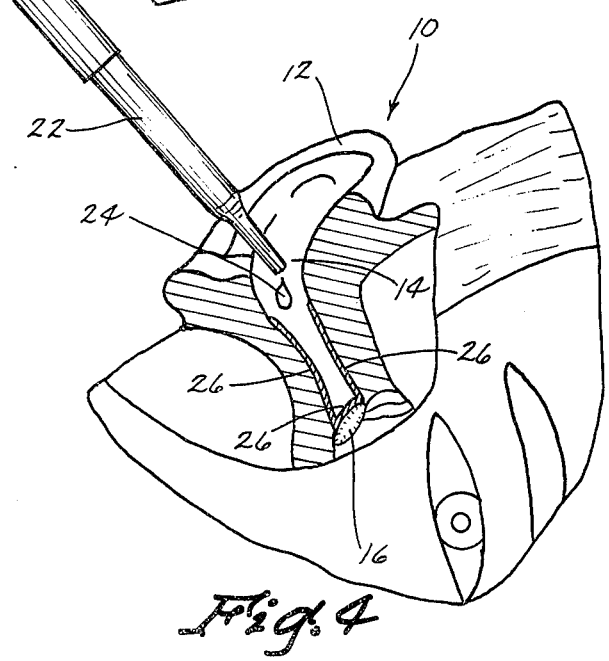
Fig. 3
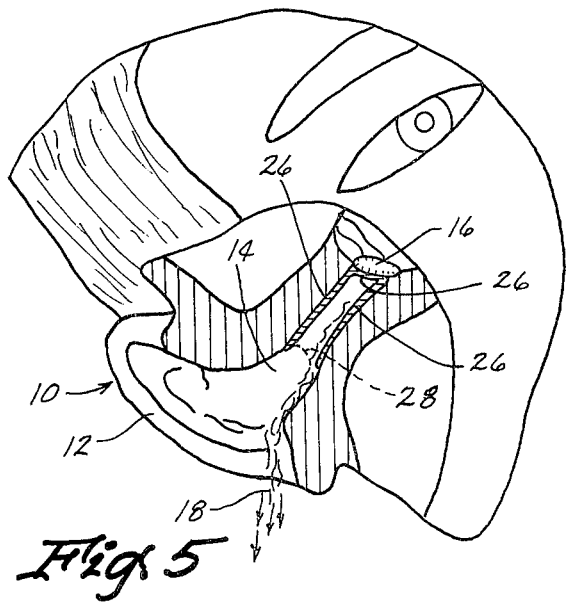
Fig. 4
Fig. 5

PREVENTIVE TREATMENT FOR OTITIS EXTERNAE

BACKGROUND OF THE INVENTION

Otitis Externae is commonly referred to as "Swimmer's Ear". It is a condition which frequently occurs following swimming. It is caused by the external auditory canal of the ear filling with water which is difficult to remove. The water is difficult to remove because it stays in the ear, and seems to defy gravity, by refusing to flow out of the ear. If the water stays in the ear for some period of time, this dark, moist and warm environment is perfect for bacteria to grow. As a result, infections by bacteria and funguses may result with the water being the primary vehicle for the beginning of the bacterial and fungus growth. The result is Swimmer's Ear.

Swimmer's Ear is characterized by diffuse inflammation of the external auditory canal wall skin and may involve the auricle. Pain is severe. Even fever may be present and the post-auricler and upper cervical lymph nodes enlarged. Occasionally, Otitis Externae may even simulate acute mastoiditis.

About one-half of the people who swim seem to have a problem with their ears filling with water. It is believed that the other one-half of the swimmers do not have this problem because of the shape of their outer ear and the volumetric size of their external auditory canal is such that the surface tension of water can be overcome so that the water will easily pour out of the ear when the head is turned to the side. However, for the other one-half of the swimmers, the size and volume of the external auditory canal seems to be just about right for surface tension resistance and capillary action to occur with the result being that water which accumulates in the ear seems to defy gravity when the head is turned to the side and will not easily pour out.

The problem of Swimmer's Ear has heretofore been approached by methods of water removal after swimming and by medicinal treatment after the condition has occurred. Typical medicinal treatments involve, after removal of the water, treating of the external auditory canal with a bacteriostatic agent or a bactericidal agent. Examples of such agents are hydrogen peroxide, isopropyl alcohol, aluminum acetate solution, boric acid and the like. In one typical treatment, aluminum acetate solution is applied on a wick placed in the external auditory canal for approximately 48 hours in order to reduce severe swelling. This is followed by ear drops containing an antimicrobial agent and a topical corticosteroid. Frequent and gentle, but thorough, mechanical cleansing is essential to remove the debris from the external auditory canal and to allow the medicament to reach the diseased tissue. In another typical treatment boric acid - isopropyl alcohol compositions are added to the ear after swimming, showering or bathing in an effort to help prevent Otitis Externae by drying up excess water.

In summary, the approach to the problem of swimmer's ear has been one of treating the ear after the condition has occurred or alternatively of treating the ear after exposure to water in an effort to remove the water.

Accordingly, it is an object of this invention to provide a preventive treatment for Otitis Externae and for eliminating the discomfort of water remaining in the external auditory canal.

Another object of this invention is to provide a preventive treatment for Otitis Externae which is not a medical treatment, but a physical treatment in order to prevent the physical phenomenon of capillary action and surface tension from occurring, both of which allow water to fill the external auditory canal and stay there to seemingly defy gravity.

Another object of this invention is to provide a method of preventive, physical treatment for swimmer's ear by treating the external auditory canal with a pharmaceutically safe, liquid, non-ionic, substantially water insoluble, aqueous surface tension reducing agent.

Another object of this invention is to prevent swimmer's ear by treatment with an aqueous tension reducing agent as described above, which has the additional property of being incapable of supporting bacterial growth.

Yet another object of this invention is to provide a water insoluble coating for the external auditory canal which provides an effective barrier against bacteria reaching the canal surface per se.

Another object of this invention is to provide a composition for preventive treatment for swimmer's ear, with the composition containing an aqueous surface tension reducing agent which may be blended with medicinal agents, such as bacteriostatic agents, bactericidal agents, and the like.

Another object of this invention is to provide a preventive treatment for swimmer's ear, which is of a proper viscosity such that it can be uniformly and easily dispensed in the form of ear drops.

The method of accomplishing these and other objects of the invention will be apparent from the detailed description of the invention which follows.

BRIEF DESCRIPTION OF THE DRAWINGS

FIG. 1 is a perspective view of a swimmer's head showing the location of the external auditory canal.

FIG. 2 is a cross-sectional view showing the outer ear, and the external auditory canal.

FIG. 3 is a view similar to FIG. 2 showing a swimmer's ear with the external auditory canal filled with water.

FIG. 4 shows a view similar to FIGS. 2 and 3 with the external auditory canal coated with an aqueous surface tension reducing agent, dispensed from a dropper.

FIG. 5 shows that the swimmer's head is tilted sideways, water in the swimmer's ear after the preventive treatment applied in FIG. 3, will only pool momentarily and then easily exit.

DETAILED DESCRIPTION OF THE INVENTION

As heretofore stated, this invention has as its object a preventive treatment for swimmer's ear which prevents water from accumulating in the ear and being retained there for prolonged periods of time. As a result, swimmer's ear is prevented along with the generally uncomfortable feeling of water filling the external auditory canal and remaining there.

Prior art treatments for this disease have approached the problem from the standpoint of treatment to remove water after the ear has filled and from the standpoint of a medicinal treatment after swimmer's ear has occurred. This invention approaches the problem from a standpoint of the physical phenomenon involved with the result being a preventive treatment which eliminates the possibility of water accumulating in the external auditory canal for any prolonged period of time.

The tendency of a liquid to decrease its surface area is referred to as surface tension. It is caused by the fact that the molecules at the surface of the liquid are pulled inward by other molecules of the liquid and as a result the liquid tends to adjust itself to a minimum surface area. This is caused by the cohesive forces of the molecules acting together.

Besides the cohesive forces of molecules, where there is an interface between a liquid and a solid, there is also another force at work called an adhesive force. This force is due to the attraction between unlike molecules, such as between a liquid and a solid surface. The result of both the cohesive force and the adhesive forces working together are, that if the adhesive force between the liquid molecules and the solid surface is greater than the cohesive force between the liquid molecules themselves, the liquid will wet the walls of the solid material, spread over it and actually rise in a column to produce what is known as capillary action.

If on the other hand, the cohesive forces are greater than the adhesive forces attracting the liquid, the liquid will not rise by capillary action, but will simply stay at the same level and be retained there by the surface tension.

FIGS. 1 and 2 shows an ear 10 along with the outer ear portion 12 and the external auditory canal 14 and the ear drum 16.

FIG. 3 shows a swimmer's ear with the ear having been filled with water 18 during the swimming activity to the level shown by the meniscus 20 of the water 18.

As the swimmer turns his head to the side, in an effort to "pour" the water out of his external auditory canal, the forces of capillary action and surface tension at the meniscus 20 cooperate to prevent the water from easily being removed from the external auditory canal. As a result, for those swimmers whose ear has the right size and volume proportions, the water in the ear seems to defy gravity and remain therein. This is caused by the cohesive forces of the water molecules and the adhesive forces between the water molecules and molecules of the skin surface of the external auditory canal 14 and ear drum 16.

The preventive treatment of this invention overcomes the physical phenomenon of surface tension and capillary action so that water 18 will only momentarily pool in the external auditory canal 14 and when the head is tilted may easily pour out of the outer ear 12.

As seen in FIG. 4, the preventive agent may be conveniently applied to the external auditory canal 14 by means of a dropper 22 by simply applying drops 24 to the external auditory canal 14. The aqueous surface tension reducing agent coats the outer skin surface of the external auditory canal 14 as depicted at 26. As seen in FIG, 5, as a result when water fills the swimmer's ear, it only momentarily pools as depicted by the meniscus 28 and runs out of the external auditory canal 14 and out of the outer ear 12.

The aqueous surface tension reducing agents which are suitable for use in the preventive treatment of this invention must meet several critical criteria. First, they must be pharmaceutically safe. That is, the aqueous surface tension reducing agent must be non-toxic, non-allergenic, and non-irritable to the skin of the users of the product. Secondly, the aqueous surface tension reducing agent must be a liquid since only liquids can be conveniently applied to the difficult to reach skin area of the external auditory canal 14. Third, the aqueous surface tension reducing agent must be a non-ionic substantially water insoluble agent. The agent must be non-ionic in order to decrease its potential for chemical reaction in the presence of chemical constituents in a swimming pool, and must be substantially water insoluble because if a water soluble agent is utilized, the agent would simply be washed out of the external auditory canal after the first dive of the swimmer into the water. Finally, the agent must be one which is capable of reducing the surface tension of an aqueous medium such that the surface active agent will overcome the phenomenon of surface tension and capillary action so that the natural gravitational action will prevail and allow water which momentarily pools in the external auditory canal 14 to be poured out when the head is tilted as shown in FIG. 5.

There are other desirable physical attributes of the aqueous surface tension reducing agent which are not critical in the sense that those previously mentioned herein are, but are in fact preferred. For example, it is preferred that the aqueous surface tension reducing agent be an agent which will not support bacterial growth, that is to say, it will not act as host environment for bacterial growth. It is also preferred that the aqueous surface tension reducing agent be one which has the capability of being blended with pharmaceutical diluents, and medicinal agents as well as bactericidal agents and bacteriostatic agents to form a miscible product.

It is also preferred that the aqueous surface tension reducing agent be an agent which has a viscosity such that it may be conveniently applied in the form of ear drops. If the surface tension reducing agent is too thick, it will be difficult to apply to the hard to reach area of the external auditory canal 14. On the other hand, if the agent is too thin, its longevity after application will be very poor.

It is preferred that the surface tension reducing agent have a viscosity within the range of from about 35 centipoises to about 4,250 centipoises, with a most preferred range being from about 1,000 centipoises, to about 3,000 centipoises. Those surface active agents meeting the other criteria of this invention falling within the most preferred range of viscosity have been found to be agents which can be easily and conveniently dispensed in the form of ear drops and which will provide a coat of surface active agent along the external auditory canal 14 of sufficient tenacity that it may stay there for the duration of an average period of swimming.

Surprisingly there are only a few presently known surface active agents which meet all of the criteria essential for this invention. Those agents which do are generally classified as surface active agents having ether linkages, ester linkages, ether-ester linkages and amide linkages. Examples of surface active agents which contain an ester or ether linkage at some point within the molecule. Examples include sorbitan fatty acid esters, polyoxyethylene sorbitol esters, polyoxyethylene alcohol, and mixed fatty acid ester blends. Examples of specific surface active agents meeting these criterion include sorbitan monolaurate, sold by ICI America, Inc. under the trademark Arlacel 20 and having a viscosity of 3,000 cs. at 25° C., sorbitan monolaurate having a viscosity of 4,250 cs. at 25° C. and sold by ICI America Inc. under the trademark Span 20.

Suitable polyoxyethylene sorbitol esters for use in the method and composition of this invention include polyoxyethylene sorbitol oleate having a viscosity at 25° C.

of 1800 cs. which is insoluble in water at 25° C. and is sold by ICI America, Inc. under the trademark Atlox 1087. Another compound falling into this category is polyoxyethylene sorbitol tall oil having a viscosity of 900 cs., an insolubility in water at 25° C. and was sold by ICI America, Inc. under the trademark Atlox 1256. Still another compound suitable for use herein falling into the general category of polyoxyethylene sorbitol esters is a polyoxyethylene sorbitol ester of mixed fatty and resin acids having a viscosity at 25° C. of 1900 cs. and is likewise insoluble in water at 25° C. This compound was sold by ICI America, Inc. under the trademark G-1234. Yet another compound falling into the class of polyoxyethylene sorbitol esters suitable for use in this invention is polyoxyethylene sorbitol tallow esters having a pour point of 18° C., and was sold by ICI America, Inc. under the trademark G-3284.

The only polyoxyethylene alcohol presently known to be usable in the process and composition of this invention is polyoxyethylene (4) lauryl ether having a viscosity at 25° C. of 35 cs. This compound is water insoluble at 25° C. and is sold by ICI America, Inc. under the trademark Brij 30. Two additional surfactants sold by ICI America, Inc. in the past, but no longer available from them but utilizable herein are polyoxyethylene mannitol dioleate, and trademarked G-2800 and sorbitan monoleate polyoxyethylene ester mixed fatty and resin acids blend having a viscosity at 25° C. of 500 cs. and being water insoluble at 25° C. is trademarked as G-2684.

Non-ionic surface active agents having an amide linkage useful in this invention are those derived from alkylol amines, for example, diethanol amine. Typically a member of this group is lauroyl diethenol amide.

At present the most preferred surface active agent is one sold by Industrial Chemical Industries under the trademark Atlox 1087. This compound is polyoxyethylene sorbitol oleate which has a viscosity at 25° C of 1800 cs.

For examples of other Atlas surfactants see the publication entitled "Atlas Surfactants Publication" No. LG-601.5M1/70, which is incorporated herein by reference. With regard to the physiological stability of the Atlas surfactants, see "Guide to the Physiological Stability of Atlas Surfactants", printing No. 100-1 (LD-146) 10M8/74, copyright 1974, which is incorporated herein by reference.

The amount of the aqueous surface tension reducing agent employed is not critical. Generally for those falling within the preferred viscosity range, one drop is sufficient to overcome the surface tension and adhesive forces; however, it is more desirable to add several drops in order to coat the canal which provides a protective outer coating of a water insoluble substance and provides an environment not conducive to bacterial growth.

As heretofore mentioned, the surface active agents may be mixed with medicinal agents, bacteriostatic agents or bactericidal agents. Examples include hydrogen peroxide, isopropyl alcohol, aluminum acetate solution, boric acid, antimicrobial agents, and topical corticosteroids. Of course, where the surface active agent is blended with a medicinal agent or other medicinal actives as described herein, the two agents must be miscible. The amount of each agent employed is well within the skill of the art and not critical. The amount of medicinal agent must be sufficient that it will perform its medicinal function and the amount of aqueous surface tension reducing agent must be such that it will also perform its physical function of reducing and minimizing the cohesive forces of surface tension and the adhesive forces of capillary action.

If desired, blends of the aqueous surface tension reducing agents may be employed in order to reach the desired viscosities for convenient application. Thus, more viscous materials may be mixed with miscible less viscous materials and so forth. Additionally, non-harmful coloring and perfuming agents may be added to provide a cosmetically attractive ear drop treatment.

EXAMPLE

A group of six swimmers known to be sufferers from swimmer's ear, and to have general problems with water filling the external auditory canal 14 during swimming, was selected. Each of these swimmers was given an unmarked eye dropper bottle and eye dropper dispenser with the bottle being filled with polyoxyethylene sorbitol oleate, an ester linkage containing aqueous surface tension reducing agent, which is a yellow liquid having a viscosity of 25° C. of 1800 cs. Polyoxyethylene sorbitol oleate is non-toxic, non-allergenic, and therefore pharmaceutically safe, is a liquid, is a non-ionic surfactant and is substantially water insoluble. It is sold by ICI Industries, Inc. under the trademark Atlox 1087. The swimmers were instructed to place one drop of the ear drops in their ear just prior to swimming. After each swimming exercise, they reported the results. None of these known sufferers from water clogged ears, had any problem during the test conducted herein. This shows that the aqueous surface tension reducing agent overcame the surface tension and capillary action of the aqueous surface medium.

an examination of the auditory canals shows that after even extended use, the composition was pharmaceutically safe to the skin surface of those treated.

Substantially similar results are obtained when other surfactants meeting the criteria herein are substituted for polyoxyethylene sorbitol oleate.

Thus, as can be seen, the invention accomplishes all of its stated objects.

What is claimed is:

1. A method of preventive treatment for swimmer's ear, and of combatting the uncomfortable feeling of water filling the ear, said method comprising,
    applying to the skin surface of the external auditory canal prior to water contact with said skin surface, a pharmaceutically safe, liquid, non-ionic, substantially water insoluble, aqueous surface tension reducing agent the amount of said surface tension reducing agent being sufficient to substantially coat said skin surface
    said aqueous surface tension reducing agent having a viscosity such that the agent can be conveniently administered as ear drops, but yet is not so thin that it will easily run out of the external auditory canal.

2. The method of claim 1 wherein said surface tension reducing agent is one which will not support bacterial growth.

3. The method of claim 1 wherein said aqueous surface tension reducing agent has a viscosity within the range of from about 35 cs. to about 4250 cs.

4. The method of claim 3 wherein said surface active agent has a viscosity within the range of from about 1000 cs. to about 3000 cs.

5. The method of claim 1 wherein said surface active agent is a surface active agent selected from the group consisting of those having an ether linkage, an ester linkage, an ester-ether linkage, and an amide linkage.

6. The method of claim 1 wherein said surface active agent is polyoxyethylene sorbitol oleate.

7. The method of claim 1 wherein a sufficient quantity of said agent is added to coat the entire skin surface of the external auditory canal to provide an effective barrier between the canal and water which enters the ear.

* * * * *